(12) United States Patent
Nardeo

(10) Patent No.: US 6,530,897 B2
(45) Date of Patent: Mar. 11, 2003

(54) STEERABLE MEDICAL CATHETER WITH BENDABLE ENCAPSULATED METAL SPRING TIP FUSED TO POLYMERIC SHAFT

(76) Inventor: Mahase Nardeo, 3842 Ashley Ct., Collegeville, PA (US) 19426

( * ) Notice: Subject to any disclaimer, the term of this patent is extended or adjusted under 35 U.S.C. 154(b) by 0 days.

(21) Appl. No.: 09/841,725

(22) Filed: Apr. 25, 2001

(65) Prior Publication Data

US 2001/0037084 A1 Nov. 1, 2001

Related U.S. Application Data

(60) Provisional application No. 60/200,442, filed on Apr. 28, 2000.

(51) Int. Cl.[7] .............................................. A61M 37/00
(52) U.S. Cl. ..................... 604/95.04; 604/528; 600/146
(58) Field of Search ................................ 604/523, 524, 604/525, 528, 95.04; 600/146–149, 434; 70/190, 210, 211, DIG. 7, DIG. 9

(56) References Cited

U.S. PATENT DOCUMENTS

| | | | | |
|---|---|---|---|---|
| 5,378,234 A | * | 1/1995 | Hammerslag et al. | 139/129 |
| 5,462,527 A | * | 10/1995 | Stevens-Wright et al. | 600/585 |
| 5,624,397 A | * | 4/1997 | Snoke et al. | 604/525 |
| 5,891,088 A | * | 4/1999 | Thompson et al. | 604/524 |
| 6,027,461 A | * | 2/2000 | Walker et al. | 600/585 |

* cited by examiner

*Primary Examiner*—Gene Mancene
*Assistant Examiner*—Patrick Buechner
(74) *Attorney, Agent, or Firm*—Volpe and Koenig, P.C.

(57) ABSTRACT

A steerable medical catheter is provided having a polymeric main shaft with a plurality of lumen extending therethrough. A flexible shaft tip portion with a metallic coil spring having a polymeric coating is located on the distal end, with the metallic coil spring being fused to the second end of the main shaft. The polymeric coating has an inner portion configured to define a plurality of lumens which extend through the coil spring. The lumens through the coil spring are aligned with the lumens in the main shaft so that they extend continuously through the catheter. The metallic coil spring is fully encapsulated by the polymeric coating and the second end of the main shaft to which it is fused. A first control wire is located in one of the lumens and affixed to the distal end.

11 Claims, 2 Drawing Sheets

STEERABLE MEDICAL CATHETER WITH BENDABLE ENCAPSULATED METAL SPRING TIP FUSED TO POLYMERIC SHAFT

CROSS-REFERENCE TO RELATED APPLICATION

This application claims the benefit of U.S. Provisional Application No. 60/200,442, filed Apr. 28, 2000.

BACKGROUND

The present invention relates to the field of steerable medical catheters for insertion into body vessels or cavities which are capable of providing access for surgical and/or medial diagnostic procedures including, but not limited to, providing a conduit for access for fiber optic cables for visualization, lasers, mechanical or electronic devices, surgical devices, or sensors capable of monitoring physiological perimeters in situ, such as pressure transducers, flow probes, oxygen sensors, or sensors for other biological or chemical parameters that might be of clinical relevance.

Instruments of this time having a relatively rigid shaft with a flexible, controllable tip are known. In these prior known instruments, the relatively rigid shaft and flexible tip are made of polymeric materials and are bonded together. Control wires extend through lumens in the shaft and are used to deflect the controllable tip in a desired direction for insertion into a body cavity or vessel. The controllable tip is made of a more flexible polymeric material than the shaft, and may include stabilizing strips encapsulated within the more flexible tip portion of the shaft to control deflection of the tip to a desired direction. However, the stabilizing strips in the flexible tip portion are not connected to the relatively rigid shaft, which places additional stress at the butt joint between the tip portion and the relatively rigid shaft.

It would be desirable to provide a more stable connection between a relatively rigid catheter shaft and a flexible tip portion. It would also be desirable to provide a means for holding a flexible tip in a desired orientation during manipulation of such a steerable medical catheter.

SUMMARY

Briefly stated, the present invention provides a steerable medical catheter. The catheter includes a polymeric main shaft having first and second ends with a plurality of lumens extending longitudinally therethrough. A shaft tip portion is provided and includes a metallic coil spring with a polymeric coating having first and second ends. The first end of the metallic coil spring is fused to the second end of the main shaft. The polymeric coating has an inner portion configured to define a plurality of lumens between the first and second ends of the coil spring which extend through the coil spring. The lumens through the coil spring are aligned with the lumens in the main shaft to provide continuous lumens through the catheter. The metallic coil spring is fully encapsulated by the polymeric coating and the second end of the main shaft to which it is fused. A first control wire is located in one of the lumens and has a first end which terminates in proximity to the second end of the coil spring and a second end which extends from the first end of the main shaft.

In another aspect, the shaft tip portion may advantageously include a terminal ring fused to the second end of the shaft tip portion. The first end of the first control wire is permanently affixed to the terminal ring, such as by welding, RF welding, adhesives, or other means. Preferably, an end cap is connected to the terminal ring.

In another aspect of the invention, an outer portion of the polymeric coating on the metallic coil spring has an outside diameter that is approximately equal to an outside diameter of the main shaft. The polymeric coating is fused to the second end of the main shaft around the coil spring to form a sealed connection such that the shaft tip portion forms a continuous, smooth extension of the main shaft. The lumens extending through the main shaft and the tip portion remain isolated from one another to provide a continuous path from the first end of the main shaft to the distal end of the catheter for each lumen.

In another aspect of the invention, a control handle is connected to the first end of the main shaft. The first control wire is connected to a rotatable steering dial located in the control handle such that rotation of the steering dial in a first direction causes the tip portion to flex in a corresponding first direction. The metallic coil spring biases the tip portion to return to a position generally axially aligned with the main shaft when the steering dial is released. Advantageously, a locking device may be provided to hold the steering dial in a desired position.

BRIEF DESCRIPTION OF THE DRAWING(S)

The foregoing summary, as well as the following detailed description of the preferred embodiments of the invention will be better understood when read in conjunction with the appended drawings. For purposes of illustrating the invention, there are shown in the drawings embodiments which are presently preferred. It should be understood, however, that the invention is not limited to precise arrangements and instrumentalities shown.

DETAILED DESCRIPTION OF THE PREFERRED EMBODIMENTS

Figure 1:
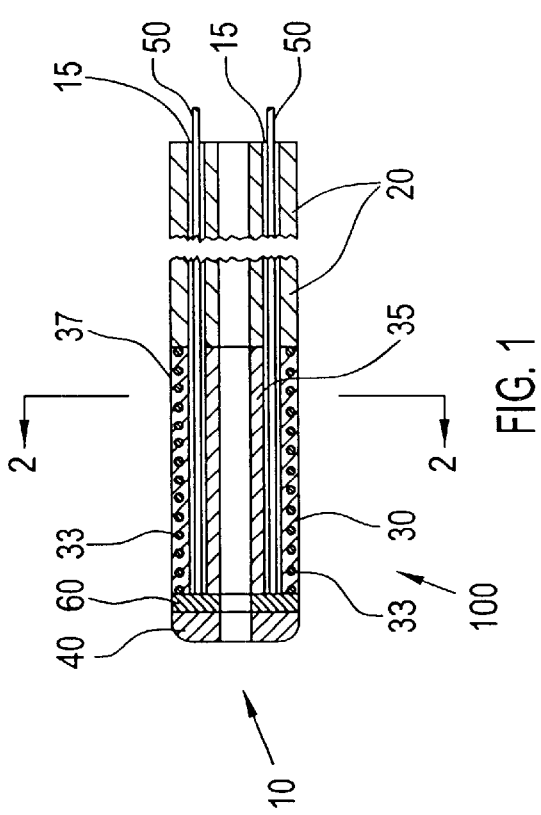
FIG. 1 is an enlarged cross-sectional view of a distal end of a catheter tip in accordance with a first embodiment of the present invention.

Certain terminology is used in the following description for convenience only and is not considered limiting. The words "right", "left", "lower" and "upper" designate directions in the drawings to which reference is made. This terminology includes the words specifically noted above, derivatives thereof and words of similar import. Additionally, the terms "a" and "one" are defined as including one or more the referenced item unless specifically noted.

Figure 2:
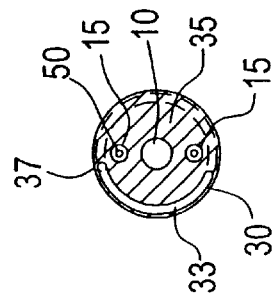
FIG. 2 is a cross-sectional view taken along lines 2—2 in FIG. 1.

Referring to FIG. 1, the present invention provides an elongated medical catheter tubing 100, a distal end of which is shown in detail, having at least one lumen 10 extending longitudinally therethrough. As shown in FIG. 1, the catheter tubing 100 comprises a main shaft 20, a flexible tip portion 30, and an end cap 40. Preferably, one or more control wires 50 extend through control wire lumen(s) 15 in the main shaft 20 and shaft tip portion 30, as shown in FIG. 2. The control wires 50 are connected to a terminal ring 60 located at the distal end of the catheter tubing 100.

In the embodiment shown in FIG. 1, the shaft tip portion 30 comprises a highly flexible metal spring 33, which is preferably a coil spring, which is located within a polymeric coating having an inner portion 35 and an external portion 37. The external portion 37 of the coating of the shaft tip portion 30 is finished such that the external surface of the catheter tubing 100 is seamless and continuous throughout the length of the end cap 40, the shaft tip portion 30 and the main shaft 20. Similarly, the inner portion 35 of the coating of the flexible tip portion 30 seals the spring 33 from leaks, and is finished to provide a seamless internal surface continuous with the lumens which extend through the main shaft 20, such that the lumens extend the length of the catheter tubing 100.

Figure 3:
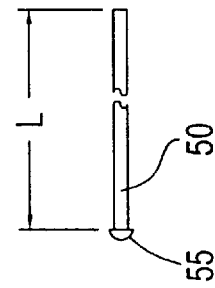
FIG. 3 is an elevational view, similar to FIG. 2, showing the terminal ring for connecting the control wires.

The control wire 50 extends approximately the entire length of the catheter tubing 100 and may be contained within the catheter lumen 10, or in separate, parallel lumens 15 within the main shaft 20 and the shaft tip portion 30. As shown in FIG. 3, for the single lumen embodiment of the present invention, the control wires 50 terminate on the terminal ring 60 where the free ends of the control wires 50 may be secured by radio frequency (RF) welding, adhesives or other means of affixing the wires to the terminal ring 60. The central aperture provided by the terminal ring 60 accommodates the main lumen 10 of the catheter without obstruction. The terminal ring 60-wire 50 assembly is incorporated between the end cap 40 and the flexible shaft tip portion 30 by RF welding.

The first end of the metallic coil spring 33 is fused directly to the second of the main shaft 20. The metallic coil spring 33 is therefore preferably fully encapsulated by the polymeric coating 35, 37 and the second end of the main shaft 20.

Figure 4:
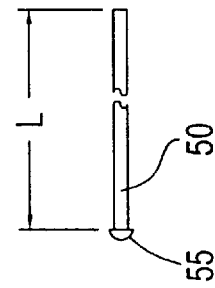
FIG. 4 is a cross-sectional view of a catheter in accordance with an alternate embodiment of the present invention having two central lumens.

Referring now to FIG. 4, an alternate dual lumen catheter embodiment of the present invention is shown. The main shaft 20' includes two central lumens 10' as well as two parallel lumens 15 for the control wires 50. The flexible shaft tip portion 30 would be configured in a similar manner providing matching lumens defined through the inner portion 35 of the polymeric coating, such that the lumens extend the length of the catheter tubing.

Figure 5:
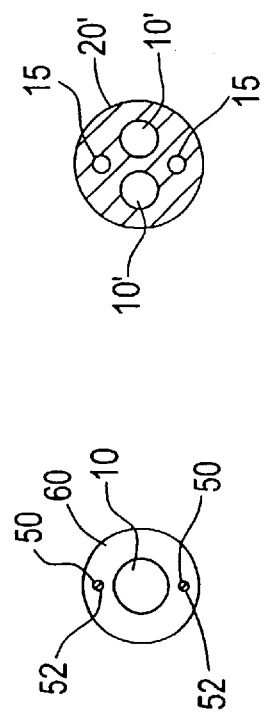
FIG. 5 is a side view of an embodiment of the control wire having a head formed at one end for use in connecting the control wire to the terminal ring.

Referring to FIG. 5, an alternate embodiment of the control wires 50 is shown. In the alternate embodiment, the control wires 50 include a mushroom head 55 which may be affixed to the wires 50 by radio frequency welding, adhesives or other affixing methods. The mushroom head is used to secure the first end of the control wire in proximity to the second, distal end of the coil spring 33.

In one preferred embodiment of the present invention, the main shaft 20 and the end cap 40 are constructed of a flexible polymeric material, such as a rigid polyurethane. One preferred material is a durometer 7033 ABS plastic, preferably PEBAX, which is compounded with 20% barium sulfate and 1% titanium dioxide. However, those skilled in the art will recognize that other suitable materials may be utilized. The metal spring 33 and control wires 50 may be constructed of any metal, but are preferably made of 304 stainless steel. The polymeric coating of the shaft tip portion 30 is preferably formed a softer durometer polyurethane material than the material of the main shaft 20. The coating may be applied to the metal spring 33 via a dipping process, with the lumens being formed in the inner portion 35 of the coating via removable mandrels located within the spring 33 during dipping. The first end of the spring 33 is then exposed for connection to the second end of the main shaft 20. The second end of the spring 33 may be encapsulated by the coating, or by being fused to the terminal ring 60, which may also be made of a polymeric material.

In the present invention, the metal spring 33 is connected directly to the second end of the main shaft 20 through fusing via a RF welding technique. This provides a polymer-to-metal fusion between the metal spring 33 and the polymeric main shaft 20 unique to the present invention, which was not previously known in the prior art, which generally utilized a polymer-to-polymer construction for connection of the flexible tip portion to the main shaft. The end cap 40 is also connected to the second end of the shaft tip portion 30 by RF welding.

As shown in FIG. 1, the junction of the flexible shaft tip portion 30 to the main shaft 20 is near the distal end of the catheter tubing 100, and the end cap 40 serves to provide a continuous plastic covering to prevent exposure of the second end of the metal spring 33, the control wires 50 or the terminal ring 60.

While the embodiments of the catheter shaft described above are preferred, they are intended to be merely exemplary and a wire variety of shapes, sizes and configurations of the inventive catheter could be utilized. For example, more or less lumens could be provided, and the shape of the catheter could be changed to any polygonal or smooth, non-circular shape as desired. Additionally, single or multiple control wires 50 could be utilized depending upon the desired functionality.

Figure 6:
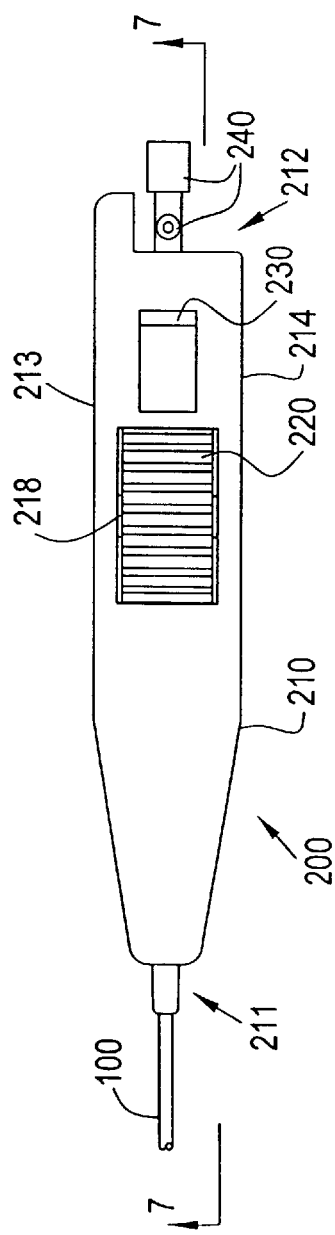
FIG. 6 is an elevational view of a control handle in accordance with the present invention connected to the catheter in accordance with the present invention.
Figure 7:
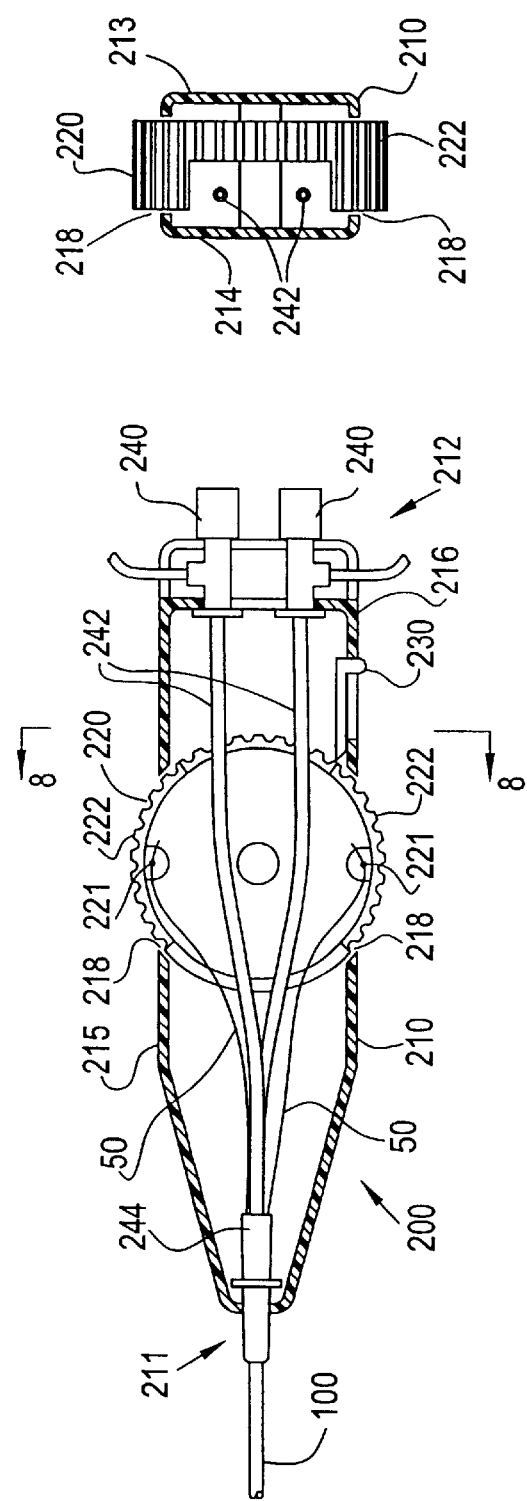
FIG. 7 is a cross-sectional view taken along lines 7—7 in FIG. 6.
Figure 8:
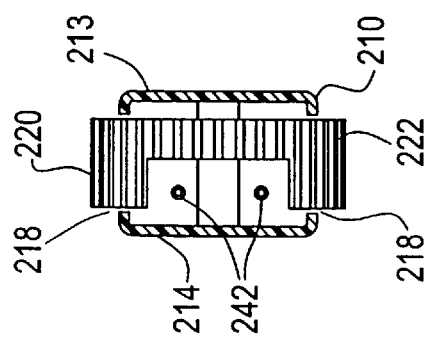
FIG. 8 is an elevational view of the rotatable steering dial taken along lines 8—8 in FIG. 7.

Referring now to FIGS. 6–8, a control handle 200 for one embodiment of the present invention is shown. The control handle 200 comprises a housing 210, a steering dial 220, a sliding locking device 230 and one or more catheter ports 240. The housing 210 has a distal end 211, from which the catheter 100 extends, and a proximal end 212, with the one or more catheter ports 240. In the preferred embodiment, the housing 210 is molded from a polymeric material, and may be constructed of a rigid ABS plastic, such as polystyrene. However, other suitable materials may also be used. The housing 210 includes a right side surface 213, a left side surface 214, a top surface 215 and a bottom surface 216. The housing 210 is ergonomically designed to be held in the hand of an operator. The distal end 211 of the control housing 210 tapers to receive the proximal end of the catheter tubing 100. The catheter lumens 10 are in communication with the catheter ports 240 via tubes 242 which extend through the housing from an end fitting 244 on the distal end of the catheter 100, to allow for access or fluid/medicament infusion therethrough.

The control wires 50 extend from the distal end of the catheter tubing 100 into the inner space defined by the housing 210. The second, distal ends of the control wires 50 terminate on opposing pins 221 located on the rotatable steering dial 220. Rotational movement of the steering dial 220 selectively pulls one of the attached control wires 50, resulting a deflection of the flexible tip portion 30 on the distal end of the main shaft 20 in a corresponding direction. Alternatively, the control wires 50 may terminate on a gear or other device mechanically controlled by motion of the steering dial 220. The steering dial 220 turns freely on an axis molded into the inner portion of the housing 210, and preferably includes gear-like teeth 222 peripherally that allow for controlled motion of the steering wheel 220 and the attached control wires 50.

One or more slots 218 are provided on the top or bottom surfaces 215, 216 of the housing 210 that allow the teeth 222 of the steering dial 220 to protrude there through for manual control by an operator. Therefore, selected rotation of the steering dial 220 provides alternating amounts of tension on the guide wires 50, thereby actuating the flexible tip portion 30 of the catheter tube 100 to move in a desired direction. The catheter 100 of the present invention thus allows for very sensitive and accurate steering that is controlled with minimal increments of rotation of the steering dial 220. While the embodiment of the control handle 200 shown in FIGS. 6–8 includes two control wires 50, it will be recognized by those skilled in the art from the present disclosure that a single control wire 50 could be utilized to bend the flexible tip portion 30 in a controlled manner in a single direction.

One or more sliding mechanisms 230 are provided on the external surface of the housing 36. The sliding mechanism 230 may be moved from a first position, out of contact with the steering dial 220, to a second position, in contact with the steering dial 220 to lock the steering dial 220 in a desired position. Preferably, the catheter ports 240 are provided with valves or caps to regulate the flow or access there through.

The above description is intended to be illustrative and not restrictive. Many modifications will be apparent to those skilled in the art based upon a reading of the above description. Accordingly, the scope of the invention should not be determined with reference to the detailed description of the preferred embodiments provided above, but should instead by determined with reference to the appended claims.

What is claimed is:

1. A steerable medical catheter, comprising:
   a main shaft made entirely of polymeric material having first and second ends with a plurality of lumens extending longitudinally therethrough;
   a shaft tip portion comprising a metallic coil spring with a polymeric coating having first and second ends, the first end of the metallic coil spring is fused to the second end of the main shaft, the polymeric coating having an inner portion configured to define a plurality of lumens between the first and second ends of the coil spring which extend through the coil spring, the lumens through the coil spring being aligned with the lumens in the main shaft such that the lumens extend through the catheter, the metallic coil spring being fully encapsulated by the polymeric coating and the second end of the main shaft; and
   a first control wire located in one of the lumens having a first end which is attached in proximity to the second end of the coil spring and a second end which extends from the first end of the main shaft.

2. The steerable medical catheter of claim 1, wherein the shaft tip portion further comprises a terminal ring fused to the second end of the metallic coil spring, the first end of the first control wire being permanently affixed to the terminal ring.

3. The steerable medical catheter of claim 2, wherein the tip portion further comprises an end cap connected to the terminal ring.

4. The steerable medical catheter of claim 1, wherein the polymeric coating is made of a material having a softer durometer than the main shaft.

5. The steerable medical catheter of claim 1, wherein an outer portion of the polymeric coating on the metallic coil spring has an outside diameter that is approximately equal to an outside diameter of the main shaft, and the polymeric coating is fused to the second end of the main shaft around the coil spring to form a sealed connection such that the shaft tip portion forms a continuous, smooth extension of the main shaft, and the lumens are isolated from one another.

6. The steerable medical catheter of claim 1, wherein the metallic coil spring is formed of stainless steel.

7. The steerable medical catheter of claim 1, further comprising a control handle connected to the first end of the main shaft, the first control wire being connected to a rotatable steering dial located in the control handle such that rotation of the steering dial in a first direction causes the tip portion to flex in a corresponding first direction, and the metallic coil spring biases the tip portion to return to a position generally axially aligned with the main shaft when the steering dial is released.

8. The steerable medical catheter of claim 7, further comprising teeth located on the rotatable steering dial, and a locking device located on the control handle movable from a first position, out of contact with the rotatable steering dial, to a second position, in contact with the steering dial to lock the steering dial in a desired position.

9. The steerable medical catheter of claim 1, further comprising a second control wire which extends through a second lumen of the plurality of lumens in the main shaft and tip portion, the second control wire being located radially opposite to the first control wire and having a first end which is attached in proximity to the second end of the metallic coil spring and a second end which extends from the first end of the main shaft.

10. The steerable medical catheter of claim 9, further comprising a control handle connected to the first end of the main shaft, the first and second control wires being connected to a rotatable steering dial located in the control handle such that rotation of the steering dial in a first direction causes the tip portion to flex in a corresponding first direction, and rotation of the steering dial in a second direction causes the tip portion to flex in a corresponding second direction, and the metallic coil spring biases the tip portion to return to a position generally axially aligned with the main shaft when the steering dial is released.

11. The steerable medical catheter of claim 10, further comprising teeth located on the rotatable steering dial, and a locking device located on the control handle movable from a first position, out of contact with the rotatable steering dial, to a second position, in contact with the steering dial to lock the steering dial in a desired position.

* * * * *